United States Patent [19]

Dorman

[11] Patent Number: 4,927,407
[45] Date of Patent: May 22, 1990

[54] CARDIAC ASSIST PUMP WITH STEADY RATE SUPPLY OF FLUID LUBRICANT

[75] Inventor: Frank Dorman, Minneapolis, Minn.

[73] Assignee: Regents of the University of Minnesota, Minneapolis, Minn.

[21] Appl. No.: 367,960

[22] Filed: Jun. 19, 1989

[51] Int. Cl.$^5$ .............................................. A61F 2/22
[52] U.S. Cl. ........................................ 600/16; 623/3; 415/112
[58] Field of Search ................ 600/16, 17; 623/3; 415/111, 112, 171.1; 277/177, 173, 179

[56] References Cited

U.S. PATENT DOCUMENTS

| | | | |
|---|---|---|---|
| 336,807 | 2/1886 | Hawley | 384/132 |
| 1,727,703 | 10/1929 | Hause et al. | 415/111 |
| 2,441,708 | 5/1948 | Luaces et al. | 417/13 |
| 2,736,265 | 2/1956 | Higgins | 415/172.1 |
| 3,487,784 | 1/1970 | Rafferty et al. | 623/3 |
| 3,608,088 | 10/1971 | Dorman et al. | 623/3 |
| 3,667,069 | 6/1972 | Blackshear et al. | 417/194 |
| 4,091,471 | 5/1978 | Richter | 623/3 |
| 4,135,253 | 1/1979 | Reich et al. | 415/112 |
| 4,224,008 | 10/1980 | Haentjens | 415/112 |
| 4,236,867 | 12/1980 | Morris | 415/112 |
| 4,239,422 | 12/1980 | Clancey | 415/112 |
| 4,276,002 | 6/1981 | Anderson | 415/112 |
| 4,328,973 | 5/1982 | Delbridge | 277/27 |
| 4,482,159 | 11/1984 | Ishitani et al. | 277/27 |
| 4,524,977 | 6/1985 | Masaaki | 277/3 |
| 4,534,570 | 3/1984 | Munde | 277/177 |
| 4,589,822 | 5/1986 | Clausen et al. | 415/112 |
| 4,625,712 | 12/1986 | Wampler | 623/3 |
| 4,704,121 | 11/1987 | Moise | 415/112 |
| 4,846,152 | 7/1989 | Wampler et al. | 623/3 |

Primary Examiner—Francis Jaworski
Assistant Examiner—George Manuel
Attorney, Agent, or Firm—Haugen and Nikolai

[57] ABSTRACT

A centrifugal pump for left ventricle assist includes a pump housing forming an impeller chamber with inlet and outlet passages and enclosing an impeller rotatable to move blood through the impeller chamber, and a rotor chamber enclosing a rotor integral with the impeller and rotatable to drive the impeller. An elastically deformable seal member separates the rotor and impeller chambers, and includes an annular lip seal surrounding a shaft which joins the impeller and rotor. A saline solution is supplied at a constant fluid flow rate to the rotor chamber through an inlet passage, and leaves the rotor chamber by perfusing into the impeller chamber along the interface between the shaft and lip seal. The saline solution thus provides hydrodynamic bearings between the rotating shaft and rotor, and the fixed pump housing and lip seal, and further prevents blood in the impeller chamber from entering the rotor chamber. The lip seal is configured to encourage flow of saline solution along the lip seal/impeller shaft interface, while resisting the flow of blood along the interface.

21 Claims, 2 Drawing Sheets

CARDIAC ASSIST PUMP WITH STEADY RATE SUPPLY OF FLUID LUBRICANT

BACKGROUND OF THE INVENTION

This invention relates to devices for conveying bodily fluids, and more particularly to body implantable left ventricle or whole heart assist pumps for bypassing the heart during open heart surgery, or to assist a disfunctional heart or left ventricle.

Centrifugal blood pumps have long been recognized for their utility as a supplement to or replacement for the human heart, for example in assisting a damaged left ventricle, for temporary heart bypass in the event that such is required in open heart surgery, and for total heart bypass when two such pumps are implanted. Such pumps operate continuously and at high speeds, for example in the range of 4,000 to 7,000 rpm, and are relatively small, which facilitates implantation.

A major problem with centrifugal blood pumps, however, is the need for a positive seal between the pump housing and the internal rotating means for pumping, e.g. the impeller and rotor. Conventional shaft seals are not effective when the involved fluid is blood, since blood is not suitable, either as a lubricant or as a cooling medium.

In recognition of these difficulties, centrifugal pumps have been designed to utilize a lubricant other than blood, for example a saline solution, along with a sealing means to prevent the passage of blood into lubricated areas. U.S. Pat. No. 4,135,253 (Reich et al) discloses an impeller pump in which a saline solution in a rotor housing floats the rotor. An elastomeric lip seal surrounds a shaft which couples the rotor and impeller. The saline solution is maintained at a positive pressure greater than the blood pressure on the opposite side of the seal, thus to prevent flow of blood into the rotor housing. However, the breaking pressure to establish a small flow across the seal is sufficiently high in some cases that the pump can start with little or no flow through the seal area. The dry seal heats and wears rapidly. Following such rapid wear, a flow of saline lubricates and cools the seal, substantially preventing further rapid wear, to initiate a slow wear phase tending to smooth the seal. The results of this wear process are unpredictable; at times satisfactory, at other times permitting excessive saline leakage into the blood stream, diluting the blood to an undesirable degree.

In U.S. Pat. No. 4,704,121 (Moise), an anti-thrombogenic blood pump features an impeller blood pump with seals lubricated by a saline solution, with saline perfusing from about a rotary impeller shaft into the blood conveying impeller chamber at a rate of about one cubic centimeter every twenty-four hours. The seal in the perfusion area can be a face seal, a cylindrical (journal) seal or a hybrid face/cylindrical seal. In each case, the seal is a restricted fluid passage between two rigid members, namely the rotating shaft and the impeller chamber wall, requiring strict tolerances for a clearance said to be typically in the order of 2.5 micrometers. Aside from high manufacturing cost, this arrangement provides no resistance to blood entry into the chamber containing the shaft in the event of any disruption in saline flow.

Therefore, it is an object of the present invention to provide a relatively low cost means for achieving an effective seal between an impeller chamber and a rotor chamber in a centrifugal blood pump.

Another object of the invention is to provide a pump for bodily fluids in which a flexible seal, deformable to permit a steady perfusion of a fluid lubricant from a rotor chamber into an impeller chamber, prevents passage of blood from the impeller chamber into the rotor chamber.

Another object is to provide a perfusion seal also effective to resist passage of blood, from an impeller chamber past the seal into a rotor chamber, in the event of a temporary interruption in the perfusion of the lubricant.

Yet another object of the invention is to provide a single source for a lubricant and fluid for a perfusion seal between the rotor and impeller chambers of a centrifugal pump, with lubricant supplied to the rotor chamber at a constant flow rate, independent of the rotational speed of the impeller.

SUMMARY OF THE INVENTION

To achieve these and other objects, there is provided a system for conveying bodily fluids. The system includes a pump having a housing defining a first chamber, a second chamber, a first inlet passageway in fluid communication with the first chamber for admitting a bodily fluid into the first chamber, a first outlet passageway in fluid communication with the first chamber for expelling the bodily fluid out of the first chamber, and a second inlet passageway in fluid communication with the second chamber for admitting a fluid lubricant into the second chamber. The lubricant is biocompatible and compatible with in the bodily fluid. An impeller is mounted rotatably in the first chamber, and a rotor is mounted to rotate in the second chamber, with a connecting means coupling the impeller for rotation responsive to rotation of the rotor. An elastically deformable sealing means is fixed to the housing between the first chamber and the second chamber, and forms an interface with the connecting means. The sealing means normally, i.e. when not elastically deformed, is in a surface engagement with the connecting means along the interface.

A supply means is provided for supplying the lubricant at a first predetermined constant flow rate through the second inlet passageway into the second chamber. This causes a perfusion of the lubricant, at a second constant fluid flow rate, along the interface and into the first chamber, thus to elastically deform the sealing means and maintain the sealing means in a close, spaced apart relation to the connecting means. The lubricant maintains the spaced apart relation in spite of a restoring force in the sealing means which, in the absence of the perfusion of lubricant, would tend to restore the surface engagement. The system further includes a drive means for rotating the rotor to convey the bodily fluids through the first chamber and first passageways.

Preferably the connecting means is a cylindrical shaft mounted to the impeller, connected to the rotor and concentric with the impeller and rotor on a common axis of rotation. The sealing means then includes a flexible lip seal which surrounds the shaft, forming an annular interface. The annular interface can provide the sole means for passage of the lubricant out of the second chamber. This eliminates the need for a separate lubricant exit passageway, but more importantly enables control of the perfusion rate of lubricant along the interface by controlling the flow rate of lubricant into the second chamber.

The sealing means includes a lip seal particularly well suited to promote flow of lubricant into the first chamber while preventing passage of blood from the first chamber into the second. In particular, the lip seal includes an annular shaft interfacing surface proximate the shaft, but spaced apart from the shaft by the thin film of lubricant resulting from the controlled lubricant flow. The lip seal further includes a tapered surface adjacent the interface surface and inclined in the direction toward the second chamber, to form an acute angle with the shaft. Consequently, fluid pressure of the lubricant acts against the lip seal tending to force it radially outward and away from the shaft, facilitating flow of the fluid lubricant past the seal.

Conversely, a chamber facing surface of the lip seal on the opposite side of the shaft interfacing surface forms at least a 90° angle with the interfacing surface. As a result, the fluid pressure of blood or other bodily fluid in the first chamber tends to force the lip seal against the shaft. Thus, the flexible lip seal substantially prevents passage of bodily fluid past the seal into the second chamber, even in the absence of the desired steady flow and positive pressure differential of the saline lubricant.

The preferred drive means includes an annular permanent magnet housed in a shell of the rotor, and an annular stator or armature fixed to the outside of the rotor casing and surrounding the shell. Electrical energy is supplied to the stator to rotate the rotor and impeller. The means for supplying the fluid lubricant is preferably a body implantable infusion pump, for example a syringe pump adjusted to provide a constant flow rate of lubricant to the rotor chamber.

A salient feature of the present invention is the supplying of the lubricant at a constant rate rather than at a predetermined pressure. The constant flow is applied prior to actuating the rotor, and increases pressure until a break pressure is reached, elastically deforming the lip seal to force it away from surface engagement with the shaft, thus to admit lubricant beyond the seal into the first chamber. An initial, rapid flow of lubricant reduces pressure at the seal to a steady-state level corresponding to a constant flow of lubricant at the rate of from 0.5 to 1000 milliliters per day, and more preferably about ten milliliters per day. This continuous, steady flow provides a thin film of lubricant between the rotating shaft and stationary lip seal, preventing wear to the lip seal previously caused by initiating the pump with a dry lip seal. The lubricant perfusion film provides a hydrodynamic bearing between the shaft and seal which virtually prevents wear, even over long-term use. Consequently, the lip seal configuration and dimensions may be precisely tailored to the shaft, with no need to provide an excess for expected wear.

IN THE DRAWINGS

Other features and advantages will become apparent upon consideration of the following detailed description and the drawings, in which.

DETAILED DESCRIPTION OF THE PREFERRED EMBODIMENT

Figure 1:
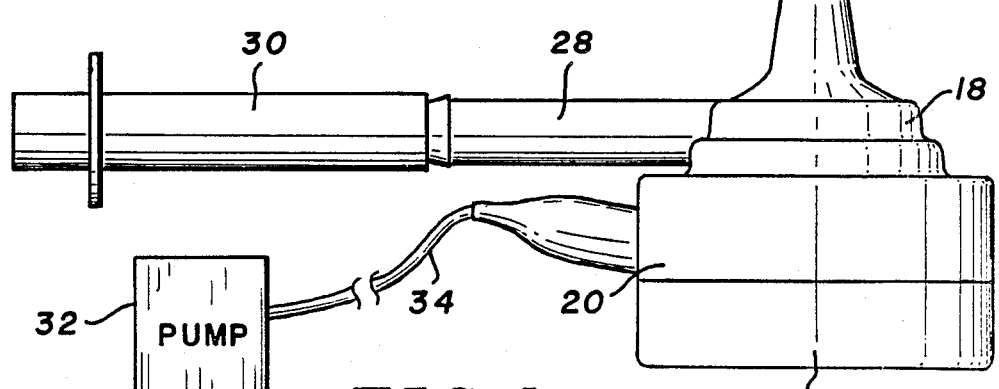
FIG. 1 is an elevational view of a left ventricle assist centrifugal pump constructed in accordance with the present invention.

Turning now to the drawings, there is shown in FIG. 1 a body implantable centrifugal pump 16 including a housing formed by joinder of an impeller casing 18 and a rotor casing 20, both casings being annular and constructed of a non-electrically conductive, biocompatible material such as polycarbonate or polysulfone. A titanium stator casing 22 surrounds the bottom portion of rotor casing 20, for securing an annular stator to the outside of the rotor casing. Alternatively, the stator and rotor casing bottom can be encapsulated in a plastic, e.g. a biocompatible epoxy. An inlet catheter or tube 24 having a plurality of inlet openings 26 receives blood or other bodily fluids into an impeller chamber defined by impeller casing 18. Bodily fluid is expelled from the chamber through an outlet tube 28 and a catheter or tube 30 connected to the outlet tube. Catheter 24 extends from the pump to the heart where the inlet with openings 26 extends into the left ventrical of the heart. Catheter 30 extends from the pump to the aorta at which point the blood returns to circulation. Catheters 24 and 30 are secured by Dacron grafts, cuffs or other appropriate means. A body implantable infusion pump 32 supplies a saline solution through a length of flexible tubing 34 to a rotor chamber formed in rotor casing 20. Infusion pump 32 preferably is a roller pump or a syringe pump powered by an internal battery to discharge saline at a predetermined, constant rate, for example by a continuous or stepped advance of a plunger in a manner well known and thus not further described herein. Implanted infusion pumps of either the constant flow type available from Infusaid or the electronic variable flow type available from Medtronic or Minimed, can be used.

Figure 2:
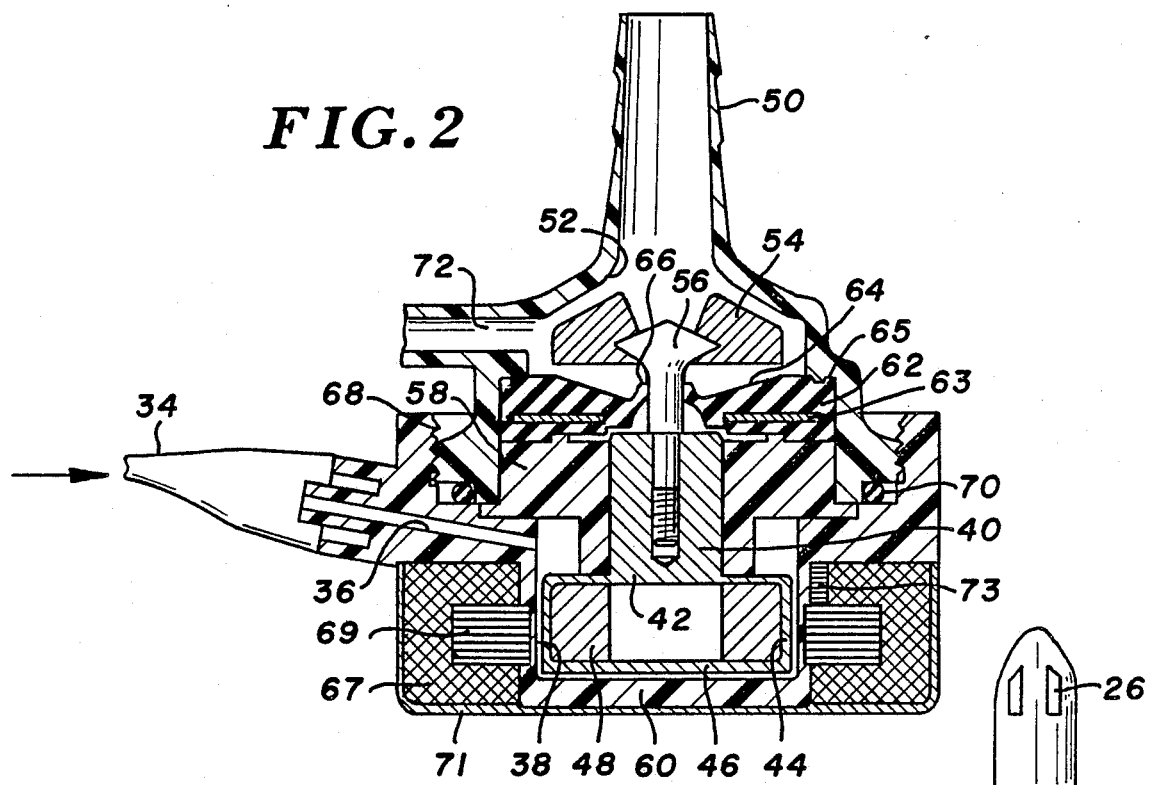
FIG. 2 is an enlarged sectional view of the centrifugal pump in FIG. 1.

As seen in FIG. 2, the saline solution is provided through a passageway 36 to a rotor chamber 38 formed by rotor casing 20. A stainless steel rotor 40 is contained to rotate within the pump housing about a vertical axis, and is generally cylindrical having an inverted T-shaped profile. Rotor 40 includes a cylindrical shank 42 and a shell 44 below the shank and somewhat larger in diameter. A disc-shaped cover 46 is secured to the shell for retaining an annular, four-pole neodymium iron (NdFe) permanent magnet 48. The magnet is sealed within the enclosure by welding cover 46, to separate the chemically reactive NdFe magnet from the saline solution, preventing corrosion of the magnet and contamination of the saline solution. Magnet 48 also is cemented in place within the shell prior to welding of the end cap to prevent free rotation of the magnet within the shell.

Impeller casing 18 includes an inlet throat 50 received into tube 24, and forms an impeller chamber 52 in which an impeller 54 is rotatably mounted. More particularly, the impeller includes a plurality of impeller blades fixed to a vertical cylindrical impeller shaft 56, which in turn is fixed to shank 42 either by a threaded connection or an adhesive, whereby shaft 56 and impeller 54 are integral with rotor 40. The impeller, shaft and rotor further are concentric on a common axis of rotation which in FIG. 2 is vertical. Shaft 56 preferably is constructed of a low temperature isotropic graphite, or alternatively polished, stainless steel. Impeller 54 is constructed of polycarbonate or polysulfone.

The radial position of the rotor shaft impeller assembly in the pump housing is determined by an annular rotor guide 58 surrounding shank 42. Rotor guide 58 is fixed relative to rotor casing 20, and preferably is constructed of polycarbonate or polysulfone, with an interior diameter slightly larger than the shank diameter. The axial position of the rotor is limited by a thrust bearing 60 molded into rotor casing 20.

Impeller chamber 52 and rotor chamber 38 are separated from one another by a flexible annular seal member 62, preferably constructed of a graphite filled elastomer, e.g. neoprene rubber, with an embedded metal annular plate 63 for increased strength and stability. The upper surface of the seal facing the impeller chamber is provided with a non-thrombogenic polyurethane layer 64 to prevent formation of blood clots along the surface during operation of the pump. Seal member 62 includes a ring seal 55 and an annular lip seal 66 immediately surrounding shaft 56. For maximum seal effectiveness at the lip seal and shaft interface, lip seal 66 and shaft 56 must be concentric. Accordingly, to facilitate a concentric positioning of the lip seal about the shaft, seal 66 and rotor guide 58 are concentrically aligned on a fixture (not shown) and fixed to one another with an adhesive. Then, impeller shaft 56 is directed through lip seal 66 and mounted in shank 42, with the shank surrounded by rotor guide 58, all prior to assembly of these members into the impeller and rotor casings. Consequently, as the rotor guide controls the radial location of shank 56, the guide likewise controls shaft 56 and maintains the shaft concentric within the lip seal. Rotor guide 58 and seal member 62 are fixed within the pump housing by virtue of a threaded engagement of the rotor casing and impeller casing as indicated at 68. A flexible ring seal 70 prevents flow of fluids into and out of the housing at the junction of the casings.

A stator 67, including an annular iron core 69 and copper wire windings 71 about the core, surrounds the lower portion of rotor casing 20 and is maintained about the casing by stator casing 22. Electrical energy selectively supplied to windings 71 generates and alters the magnetic field in a known manner to rotate magnet 48, and thus the rotor, impeller and shaft, at a predetermined speed, e.g. in the range of about 4,000 to 7,000 rpm. Hall sensors 73 on the stator are used to sense the angular position of magnet 48 with respect to the stator, to control the electrical current applied to the stator coils.

Operation of pump 32 involves two fluid paths. The first concerns passage of blood through inlet throat 50 into the impeller chamber, where it is expelled from the chamber through an exit conduit 72 by rotation of impeller 54. The second fluid path involves the constant flow of the saline solution into rotor chamber 38 through passageway 36. In filling the rotor chamber, the saline solution provides a fluid lubricant between the movable rotor and shaft, and the fixed rotor casing, rotor guide and seal member. In particular, the saline solution provides hydrodynamic bearings between the stationary and rotating parts, e.g. face seals or bearings between cover 46 and thrust bearing 60, an annular face seal between rotor guide 58 and shell 44, and journal bearings between the rotor guide and shank 42, and between the shell and rotor casing 20. Finally, the saline solution forms an annular journal bearing between impeller shaft 56 and lip seal 66. While a saline solution is frequently preferred, other fluid lubricants compatible with bodily fluids may be used in lieu of a saline solution.

To prevent passage of blood from impeller chamber 52 into rotor chamber 38, the saline solution is caused to perfuse past lip seal 66 into the impeller chamber at a constant perfusion rate. Further, as the passage into the impeller chamber is the sole path for saline out of rotor chamber 38, the perfusion rate is equal to the rate at which the lubricant is supplied to the rotor chamber by infusion pump 32. This simplifies construction of the centrifugal pump housing in eliminating the need to provide a separate exit passage for the lubricant fluid. Moreover, it provides for positive, direct control of the saline solution seal perfusion rate through control of the infusion pump.

Figure 3:
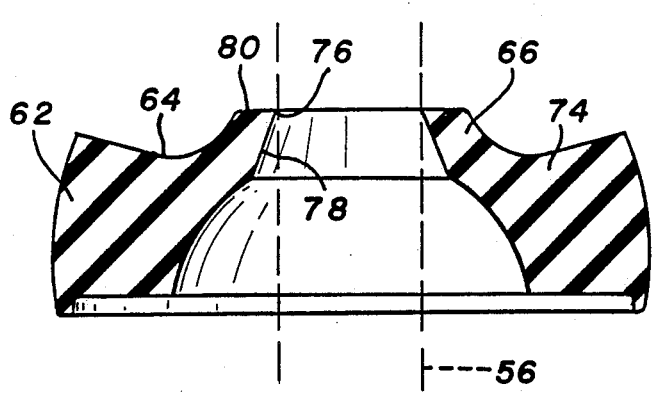
FIG. 3 is a further enlarged view of a seal contained in the pump.

As seen in FIG. 3, the configuration of seal member 62 is particularly well suited to facilitate passage of fluid lubricant upwardly into the impeller chamber, while substantially preventing passage of blood downwardly into the rotor chamber. Near lip seal 66, seal member 62 includes a narrowed annular neck 74 which allows for a slight misalignment of impeller shaft 56 with respect to the seal member, and encourages the elastic flexure or deformation of the seal necessary for lubricant perfusion. Lip seal 66 includes a relatively small, annular and vertical interfacing surface 76 with a diameter slightly smaller than the outer diameter of shaft 56. Consequently, in the absence of saline solution flow, the interface surface contacts impeller shaft 56 to form an annular interface between lip seal 66 and the shaft. A tapered surface 78 next to the interface surface is inclined away from shaft 56, in the direction towards rotor chamber 38 or downwardly as viewed in FIG. 3, at an acute angle preferably less than 45°. By contrast, an upper surface 80, on the opposite side of surface 76 and facing into impeller chamber 52, is substantially normal to the impeller shaft. As a result, fluid pressure exerted by saline solution between lip seal 66 and shaft 56 includes a substantial transverse component (horizontal as viewed in FIG. 3) which tends to separate the lip seal from the shaft and permit flow of the lubricant past the lip seal. By contrast, fluid pressure due to blood in the impeller chamber, acting upon upper surface 80, tends to close the seal. Moreover, the combination of forces due to blood upon the upper surface and neck 74, tend to maintain the lip seal closed or in surface engagement with the shaft in the absence of saline perfusion. This substantially prevents entry of blood or other bodily fluid into the rotor chamber, even in the event of temporary loss of positive saline fluid pressure.

Lip seal 66 "normally" is in surface engagement with impeller shaft 56, in the sense that such surface engagement exists in the absence of lubricant perfusion. However, under pump operating conditions, a steady perfusion of saline solution provides a thin film surrounding the shaft and maintaining the lip seal in a close but spaced apart relation to the shaft. The seal clearance can be calculated from the following equation for flow in an annular gap:

$$Q = \frac{\pi D b^3 (\Delta Pg)}{vpL}$$

where
Q=cc/sec.
D=mean shaft diameter
b=radial clearance space v=viscosity of fluid
p=density of fluid
L=length of seal
ΔPg=pressure (differential across gap)

When solved for the dimension and fluids used, and for a nominal pressure of 8.7 psi and a flow rate of one cc/day, the radial clearance is 2.26 um. This is on the order of the size of the red blood cells that must be excluded from the seal. Any interruption in saline flow would permit lip seal 66 to engage the shaft once again in response to restoring forces in the lip seal.

The flexibility of seal member 62 thus provides for an annular gap between shaft 56 and lip seal 66 which can vary in size responsive to lubricant fluid pressure, or can close altogether in the absence of such pressure. This feature provides an effective seal against entry of blood into the rotor chamber in the event the perfusion of saline is interrupted. It also reduces manufacturing cost in avoiding the strict tolerances for such passages when formed by rigid walls. Moreover, the flexible seal facilitates adjustment of the lubricant flow rate over a wider range, limited only by the maximum advisable perfusion of saline into the blood stream, but otherwise variable for measured delivery of medication, e.g. heparin or another anticoagulant.

Figure 4:
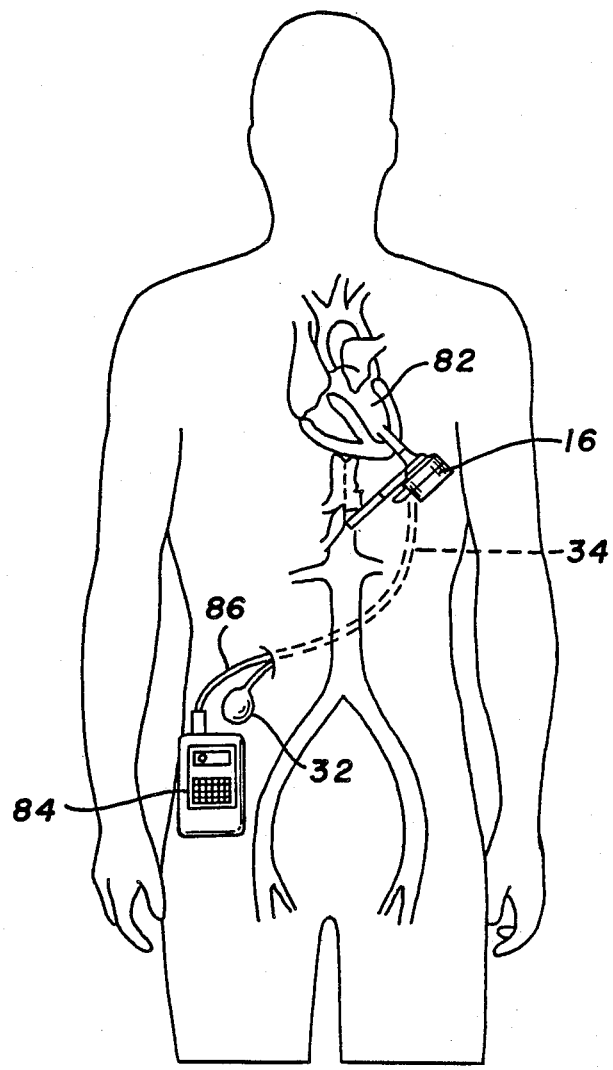
FIG. 4 is a diagrammatic view of a left ventricle assist system employing the centrifugal pump of FIG. 1.

FIG. 4 illustrates the use of centrifugal pump 16 as part of a system for assisting a left ventricle 82 of the heart. Pump 16 is implanted in the chest cavity, preferably near the heart apex, with inlet tube 24 inserted directly into the left ventricle to receive blood entering that ventricle. Outlet tubing 30 is inserted into the abdominal aorta above the renal arteries. Infusion pump 32 is outside the body as shown, or alternatively can be implanted below centrifugal pump 16, where it may be refilled with lubricant solution or medication, percutaneously with a syringe. A control unit 84, outside of the body, provides the necessary electrical energy over a line 86 to the stator for driving the pump. As an alternative to the arrangement shown, implantable infusion pump 32 can be replaced by a syringe or roller pump mounted within the control unit, in which case line 86 provides a conduit for the fluid lubricant as well.

Prior to operating centrifugal pump 16, infusion pump 32 is operated to supply saline solution through tubing 34 into rotor chamber 38, in an amount sufficient to fill the rotor chamber and perfuse across the interface between the impeller shaft and lip seal. Thus, the lip seal and shaft are adequately lubricated prior to operating pump 16, to eliminate wear and overheating of the lip seal, shaft and proximate blood or other bodily fluid. Perfusion continues at a steady rate controlled by infusion pump 32 during operation of centrifugal pump 16, and thus the fluid expelled into the abdominal aorta is a combination of bodily fluid and the saline solution.

Infusion pump 32, as previously mentioned, supplies the lubricant at a constant rate rather than at a constant pressure. Thus, pressure of the saline solution builds to a break pressure necessary to separate the initially contiguous shaft and lip seal, with a rapid initial saline flow reducing pressure until steady-state values for flow rate and pressure are achieved. Saline delivery is not pressure dependent and can be delivered at a selectively increased or decreased rate for supplying a particular medication. At the same time, pressure in the rotary chamber, particularly near the lip seal, can be monitored as a means for monitoring the lubricant fluid flow. Thus, in accordance with the present invention a steady perfusion of saline across an interface between a rotating shaft and a flexible lip seal, effectively lubricates the shaft and seal while preventing passage of blood across the seal.

What is claimed is:

1. A system for conveying bodily fluid including:
a pump having a housing defining a first chamber, a second chamber, a first inlet passageway in fluid communication with said first chamber for admitting a bodily fluid into said first chamber, a first outlet passageway in fluid communication with said first chamber for expelling said bodily fluid out of the first chamber, and a second inlet passageway in fluid communication with said second chamber for admitting a fluid lubricant into the second chamber, said lubricant being biocompatible and soluble in said bodily fluid;
an impeller mounted rotatably in said first chamber, a rotor mounted to rotate in said second chamber, and a connecting means for coupling said impeller to rotate responsive to rotation of said rotor;
an elastically deformable sealing means fixed to said housing, disposed between said first chamber and said second chamber, and forming an interface with said connecting means, said sealing means normally in a surface engagement with said connecting means along said interface;
a supply means for supplying said lubricant at a first predetermined constant fluid flow rate through the second inlet passageway into said second chamber, to cause a perfusion of said lubricant along said interface and into said first chamber at a second constant fluid flow rate, thus to elastically deform said sealing means and maintain said sealing means in close, spaced apart relation to said connecting means against a restoring force in said sealing means tending to restore said surface engagement, so long as said perfusion continues; and
a drive means for rotating said rotor to convey said bodily fluid through said first chamber and said first inlet and outlet passageways.

2. The system of claim 1 wherein:
said connecting means comprises a cylindrical shaft mounted to said impeller and to said rotor and concentric with said impeller and rotor on a common axis of rotation; and
wherein said sealing means includes a flexible lip seal surrounding said shaft, whereby said interface is annular.

3. The system of claim 2 wherein:
said annular interface provides substantially the sole means for passage of said lubricant out of said second chamber, said first and second constant fluid flow rates being substantially equal.

4. The centrifugal pump of claim 3 wherein:
said first and second constant fluid flow rates are within the range of from about 0.5 to 1000 milliliters every twenty-four hours.

5. The centrifugal pump of claim 4 wherein:
said constant fluid flow rate is approximately ten milliliters every twenty-four hours.

6. The system of claim 3 wherein:
said lip seal includes an annular shaft interfacing surface proximate said shaft, and a tapered surface adjacent said interface surface and inclined in the direction toward said second chamber to form an acute angle with said shaft.

7. The system of claim 6 wherein:

said lip seal further includes a chamber facing surface adjacent said shaft interfacing surface on the opposite side thereof from said tapered surface and forming approximately a 90° angle with said interfacing surface.

8. The system of claim 2 wherein:
said housing includes a substantially rigid impeller casing surrounding said impeller and said sealing means, and a substantially rigid rotor casing surrounding said rotor.

9. The system of claim 8 wherein:
said impeller casing and rotor casing are threadedly engaged.

10. The system of claim 8 further including:
a substantially rigid annular rotor guide member, wherein said rotor includes a cylindrical shank concentric with and receiving said shaft, and an encasing segment having a diameter larger than that of said shank, said guide member having a cylindrical opening slightly larger than the diameter of said shank, said guide member further being mounted within and integral with said rotor casing, and surrounding said shank.

11. The system of claim 10 wherein:
said sealing means is a unitary annular seal substantially spanning said impeller chamber.

12. The system of claim 11 wherein:
said seal and said guide member are fixed to one another to axially align them prior to their installation into said housing.

13. The system of claim 10 wherein:
said encasing segment of said rotor contains an annular permanent magnet, and wherein said drive means includes a stator mounted with respect to said rotor casing and proximate said encasing segment.

14. The system of claim 13 wherein:
said stator is annular and surrounds said encasing segment.

15. The system of claim 14 wherein:
said stator surrounds and is fixedly mounted to the outside of said rotor casing.

16. The system of claim 2 wherein:
said means for supplying the lubricant includes a body implantable perfusion pump including means for containing a supply of said lubricant and adapted to receive said lubricant percutaneously, and a conduit means for conveying lubricant from said containing means to said second inlet passageway at said first fluid flow rate responsive to operation of said infusion pump.

17. The system of claim 16 wherein:
said lubricant supply means comprises a roller pump.

18. The system of claim 16 wherein:
said lubricant supply means comprises a syringe pump.

19. The system of claim 2 wherein:
said lubricant supply means includes an infusion pump and a lubricant supply externally of the body, and a conduit means for conveying lubricant from said lubricant supply to said second inlet passageway at said first flow rate responsive to operation of said infusion pump.

20. The centrifugal pump of claim 1 wherein:
said bodily fluid comprises blood, and said lubricating fluid comprises a saline solution.

21. The centrifugal pump of claim 1 wherein:
said second fluid flow rate is in the range of from about 0.5 to 1000 milliliters every twenty-four hours.

* * * * *